(12) United States Patent
Shofner et al.

(10) Patent No.: US 6,598,267 B2
(45) Date of Patent: Jul. 29, 2003

(54) FIBER LENGTH AND STRENGTH MEASUREMENT SYSTEM

(75) Inventors: Christopher K. Shofner, Knoxville, TN (US); Frederick M. Shofner, Knoxville, TN (US); Frederick M. Shofner, II, Knoxville, TN (US)

(73) Assignee: Shofner Associates, Inc., Knoxville, TN (US)

( * ) Notice: Subject to any disclaimer, the term of this patent is extended or adjusted under 35 U.S.C. 154(b) by 0 days.

(21) Appl. No.: 10/116,254

(22) Filed: Apr. 4, 2002

(65) Prior Publication Data

US 2002/0157164 A1 Oct. 31, 2002

Related U.S. Application Data

(63) Continuation-in-part of application No. 09/663,497, filed on Sep. 15, 2000, now Pat. No. 6,397,437.
(60) Provisional application No. 60/281,301, filed on Apr. 4, 2001, and provisional application No. 60/304,826, filed on Jul. 12, 2001.

(51) Int. Cl.[7] .................................................. D01B 3/04
(52) U.S. Cl. ...................... 19/66 CC; 19/65 R; 19/66 R
(58) Field of Search ........................... 19/66 CC, 65 A, 19/65 R, 200, 202, 203, 204, 205, 115 R; 73/159, 160, 826, 828, 830; 356/73.1

(56) References Cited

U.S. PATENT DOCUMENTS

| 3,057,019 A | | 10/1962 | Hertel |
| 5,167,150 A | * | 12/1992 | Shofner et al. ................ 73/160 |
| 5,361,450 A | | 11/1994 | Shofner et al. |
| 5,367,747 A | * | 11/1994 | Shofner et al. ............. 19/65 R |
| 5,483,844 A | | 1/1996 | Shofner et al. |
| 5,491,876 A | | 2/1996 | Shofner et al. |
| 5,537,868 A | | 7/1996 | Shofner et al. |
| 5,842,373 A | * | 12/1998 | Stein et al. .................... 73/160 |
| 5,890,264 A | * | 4/1999 | Shofner et al. ................ 19/205 |
| 5,907,394 A | * | 5/1999 | Ghorashi et al. ........... 356/73.1 |
| 5,920,961 A | * | 7/1999 | Hollingsworth ............... 19/100 |
| 6,029,316 A | | 2/2000 | Shofner et al. |
| 6,085,584 A | * | 7/2000 | Ramachandran et al. ..... 73/159 |

FOREIGN PATENT DOCUMENTS

WO    WO 01/20321    3/2001

* cited by examiner

*Primary Examiner*—Gary L. Welch
(74) *Attorney, Agent, or Firm*—Pitts & Brittian, P.C.

(57) ABSTRACT

Method and apparatus for the collection of samples of staple fibers from a quantity (batch) of such fibers without material consideration of the "condition" of the fibers within the batch, (e.g., the relative humidity and/or temperature of the environment immediate the batch of fibers), and thereafter physically converting each sample of fibers to a tapered beard geometry, employing a rotary carrier. Each beard is grasped at one end thereof with the fibers thereof extending unsupported therefrom. The beard is conveyed to a location proximate the entrance to an air flow channel whereupon conditioned air flowing into the flow channel moves along, over and past the beard, causing the free ends of the fibers to enter the flow channel and become aligned generally along the length of the flow channel. Continued flow of conditioned air into and through the flow channel, hence in a direction generally parallel to the length of the fibers which make up the beard, ultra-rapidly conditions only the fibers of the beard. Air flow rates may reach hundreds or even thousands of ft/sec velocity within the flow channel and conditioning of the fibers may be accomplished within a matter of seconds. Withdrawal of the beard from the flow channel is sensed as a part of length testing of the fibers of the beard. Other test modules may be employed.

29 Claims, 10 Drawing Sheets

FIBER LENGTH AND STRENGTH MEASUREMENT SYSTEM

CROSS-REFERENCE TO RELATED APPLICATIONS

This application is a continuation in part of U.S. application Ser. No. 09/663,497 filed Sep. 15, 2000 now U.S. Pat. No. 6,397,437 and U.S. Provisional Applications Serial No. 60/281,301, filed Apr. 4, 2001 and Ser. No. 60/304,826, filed Jul. 12, 2001.

STATEMENT REGARDING FEDERALLY SPONSORED RESEARCH OR DEVELOPMENT

Not Applicable

BACKGROUND OF THE INVENTION

1. Field of Invention

This invention relates to the sampling of staple fibers from a batch thereof and subsequent preparation, conditioning and testing of the length and strength of the fibers in the sample. Improved length and strength data are needed for determining the performances and economic values of the fiber for processing into yarns and into knitted, woven and nonwoven fabrics or paper.

Staple fiber refers generally to non-continuous fibers whose maximum lengths range from less than one inch to several inches. Natural staple fibers include cotton, wool, flax, and other like fibers. Chopped rayon, nylon, polyester and other man-made fibers also fall into the classification of staple fibers. Also included among staple fibers are cellulose-based fibers employed in papermaking.

The economic values of staple fibers depend upon their length and strength characteristics, since these and other characteristics determine the technical performance characteristics and economic values of yarns and fabrics constructed therefrom. Length and strength characteristics include statistical properties which reflect the variations in the distributions of lengths and strengths found in bulk or batch samples of staple fibers. For natural fibers, these statistical variations can be very significant. It follows that the length or strength data products measured require careful attention to technical aspects of sampling, sample preparation, including conditioning, and measurement. Similarly, the economic consequences of the measurements and the full costs of said measurements must also be carefully considered.

For examples, in some applications the longest 2.5% of the fibers in the fiber length distribution are most important economically, in a positive sense. That is, longer fibers are more valuable, as they enable manufacture of stronger and more even yarns. For other applications the weight fraction of fibers less than 0.5 inch (so-called short fiber content) are most important economically, in a negative sense. That is, high SFC cotton can yield unacceptable yarns and fabrics. Similar considerations apply to strength data products. For both length and strength testing, improved measurements are needed, plus it is increasingly important that the measurements be done not only in special, expensive, conditioned laboratories by trained personnel but in general, unconditioned environments by unskilled personnel.

Staple fibers, and cotton fibers particularly, are commonly classed employing standards supported by many national and international governmental and non-profit organizations. The United States Department of Agriculture's Agricultural Marketing System is the leading organization, world-wide, which employs prior art instruments, such as HVI=High Volume Instruments, to measure length and strength of cotton fibers. There are important economic consequences to these measurements. The International Textile Manufacturer's Federation is another organization which evaluates and recommends fiber quality measurement systems for its members, primarily through its Working Groups on fiber quality measurements. Both USDA and ITMF have suggested that improved measurement technologies are needed to correct said measurement deficiencies in HVI and other prior art instruments and to correct certain aberrations in the marketing system. Accordingly, this invention, and inventions by some of the same inventors described in co-pending patent applications, seek to offer such improvements.

The focus of this application is improved measurement of Length and Strength. With regard to Length and Strength, prior art technologies are inherently deficient in representativeness of the fibers sampled and in precision and accuracy of the measurements, particularly in the areas of short fiber content and strength and elongation of fibers. Prior art methods are most particularly deficient in the areas of testing sample specimens which are properly equilibrated with respect to moisture content or, more accurately, equilibrated with respect to those data products which are sensitive to moisture content of the fibers. Further, such known apparatus and methods are themselves unnecessarily expensive and require relatively sophisticated test personnel and expensive, conditioned laboratories. Accordingly, the broadest objectives of our invention are to provide for less biased, more accurate and more precise measurements of Length and Strength on ultra rapidly conditioned specimens in an internal environment, such that the instrument can be cost-effectively operated in non-conditioned environments and by unskilled personnel.

2. Description of the Related Art

WO 01/20321, "Conditioning and Testing Cotton Fibers", published Mar. 22, 2001, the entire content of which is incorporated herein by reference, discloses, among other things, novel ultra rapid sample conditioning methods using combinations of water in aerosolized state (particles, with and without chemical additives) and gaseous state (molecules, but not necessarily steam). That pending application also discloses the need for careful attention to the preparation of samples of cotton fibers preparatory to and in the course of their being tested. In particular, it is also noted in that publication that the "historical" testing environment for cotton fibers of 65% relative humidity and 70 degrees F. (21 degrees C.) dry bulb temperature is of importance within the testing environment as opposed to the laboratory overall environment.

Numerous other patent and open literature references are relevant to this disclosure. U.S. Pat. No. 6,029,316 discloses methods and a machine for "rapidly" conditioning so-called "Classer's or HVI Samples" of cotton fiber prior to testing. U.S. Pat. No. 5,537,868 discloses conditioning the "Testing Zone" of fiber quality instruments with known air conditioning methods. U.S. Pat. No. 5,361,450 discloses conditioning internal "Processing Zones" of processing equipment, not testing instruments, and with known air conditioning means. U.S. Pat. Nos. 5,491,876 and 5,483,844 disclose needle sampling means for single fiber testing, not the tapered beard specimen disclosed herein. U.S. Pat. No. 3,057,019 discloses the well-known "Hertel" sampler which is still used today. These patents are incorporated herein in their entirety by reference. Distinguishing features between them and the instant invention will be made at the appropriate points in this disclosure.

Sampling of staple fibers commonly involves withdrawing a "beard" of fibers from a mass (batch) of the fibers. A "beard" is formed when fibers from a batch of staple fibers are grasped by a needle or needles or by a clamp, then combed and brushed to straighten and parallelize the fibers. Several fiber length statistics can be derived from this beard. One such fiber length is the average length of the longer one-half of the fibers (upper half mean length) and is customarily reported in both 100ths and 32nds of an inch for cotton fibers. Another is Mean Length. another, Short Fiber Content, is provided.

Fiber strength is reported in terms of grams per tex, not in force per unit area, as for metals or other materials of construction. A tex unit is equal to the weight in grams of 1,000 meters of fiber. Therefore, the strength reported in the maximum force in grams required to break a bundle of fibers one tex unit in size. Strength measurements can be made on the same beards of fibers that are used for measuring fiber length.

Our measurements of length and strength only generally follow known art. The improvements disclosed herein relate primarily to internal, ultra rapid conditioning of the beards, to less-biased sampling effected by single needles and multiple, closely-spaced needles, to improved sensing of the beard's length and strength characteristics, and to rotary motions of the sampling needles.

BRIEF SUMMARY OF THE INVENTION

The present invention comprises a method and apparatus for the collection of samples of staple fibers from a quantity (batch) of such fibers without material consideration of the "condition" of the fibers within the batch,(e.g., the relative humidity and/or temperature of the environment immediate the batch of fibers), and thereafter physically converting each sample of fibers to a tapered beard geometry. Each beard is grasped at one end thereof with the fibers thereof extending unsupported therefrom. The beard is conveyed to a location proximate the entrance to an air flow channel whereupon conditioned air flowing into the flow channel moves along, over and past the beard, causing the free ends of the fibers to enter the flow channel and become aligned generally along the length of the flow channel. Continued flow of conditioned air into and through the flow channel, hence in a direction generally parallel to the length of the fibers which make up the beard, ultra-rapidly conditions only the fibers of the beard. Air flow rates may reach hundreds or even thousands of ft/sec velocity within the flow channel and conditioning of the fibers may be accomplished within a matter of seconds.

In accordance with one aspect of the present invention, the flow of conditioned air from the flow channel, preferably is recycled to the source of conditioned air, which is located remote from the flow channel.

Within the flow channel, the strength of the fiber is tested. Thereupon, the beard is withdrawn from the flow channel and conveyed to a strength test station. In one embodiment, the flow of conditioned air is at least partially diverted toward a strength test station from which this conditioned air is captured and recycled to the source thereof. Notably, in the present invention, only that air which enters the flow channel and/or which may flow past the strength test station is conditioned, the environment associated with the fiber batch, the collection of a sample of fibers from the batch, the physical treatment of the collected sample of fibers to form a tapered beard of the fibers and substantially all locations other locations aside from the flow channel and proximate the strength test station of the apparatus is at ambient relative humidity and temperature.

In accordance with another aspect of the present invention, the physical collection of the samples from the batch of fibers includes a rotating carrier, such as a hollow cylinder having one or more collector needles mounted on the outer circumference thereof. This carrier is rotated about its longitudinal axis with such axis being oriented radially of a plurality of beard preparation stations and at least one test station whereby the collection, preparation and testing of the beard is effected at locations spaced about the circumference of the carrier. This arrangement provides for reversal of the direction of rotation of the carrier to effect selective extent of entry of the beard into the flow channel, withdrawal of the beard from the channel and conveyance thereof to a further test station, for example, and eventual reversal of the direction of rotation of the drum for removal of the beard from its collector so that the collector is cleaned of fibers in preparation for its subsequent movement through the batch of fibers and collection of a further sample of such fibers.

BRIEF DESCRIPTION OF THE SEVERAL VIEWS OF THE DRAWINGS

The above-mentioned features of the invention will become more clearly understood from the following detailed description of the invention read together with the drawings in which.

DETAILED DESCRIPTION OF THE INVENTION

Figure 1:
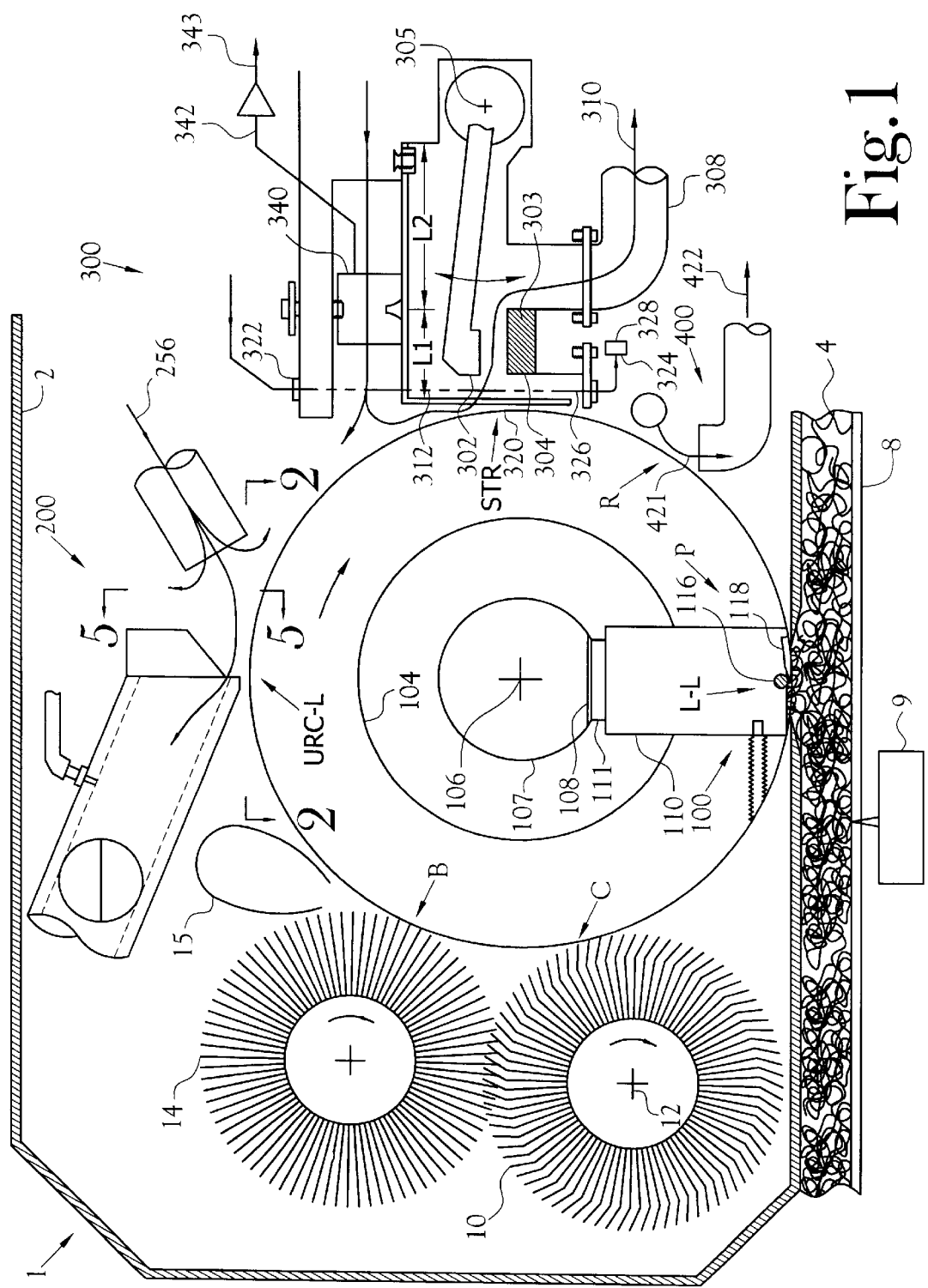
FIG. 1 is a side elevational representation of one embodiment of apparatus useful in carrying out the method of the present invention.
Figure 2:
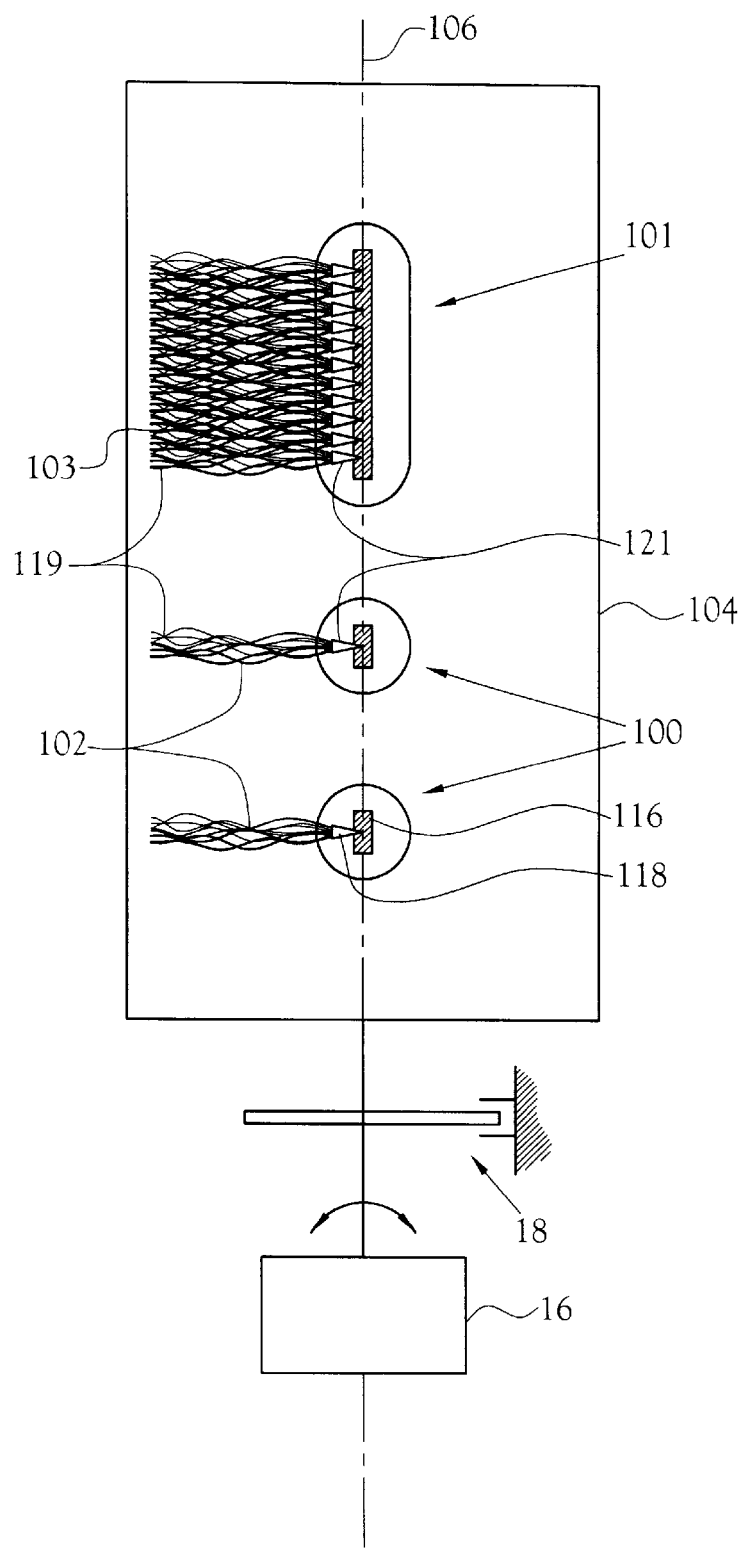
FIG. 2 is a top view of the needle-carrying carrier of the apparatus of FIG. 1 and is taken generally along line 2—2 of FIG. 1.

FIGS. 1 and 2 are end and top views of the main parts of an apparatus and method and system 1 for making improved length and strength measurements. Apparatus 1 is called the "Length +Strength Module," being one module of several on a common instrument platform called "RapidTester." These parts and other assemblies are contained within environmental enclosure 2 and consist of needle samplers 100, 101 mounted into needle roll 104. Needle roll or cylinder 104 rotates around axis 106 and positions single needle samplers 100 or multiple needle samplers 101 with respect to various stations around needle roll 104, where various operations and measurements are performed. This rotational positioning is key to the operations and measurements. Other key elements of the invention are tapered bundles or beards of fibers 102, 103, seen best in FIG. 2, and upon which the operations and measurements are made.

Figure 3:
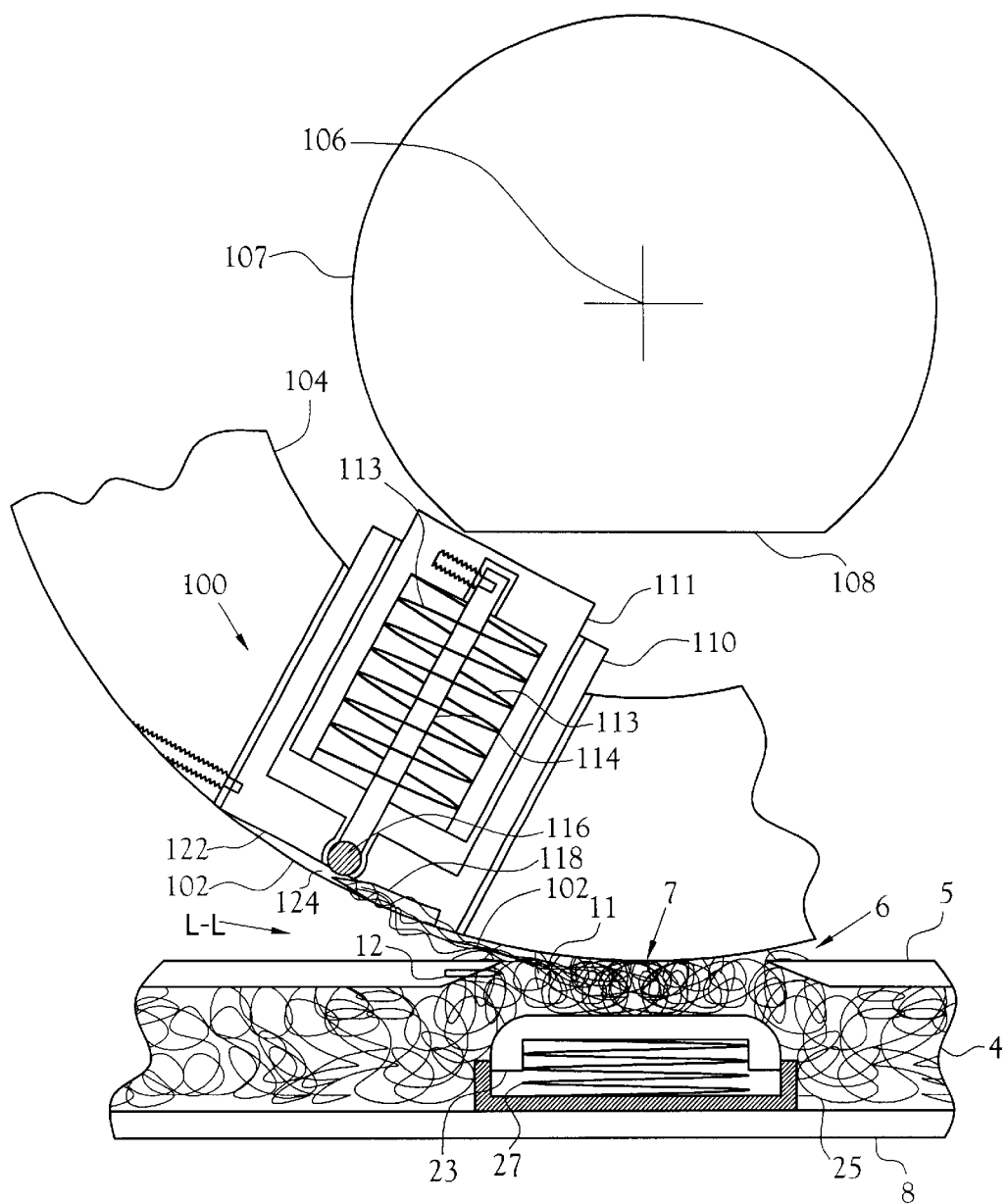
FIG. 3 is an enlarged representation of one embodiment of a portion of the carrier depicted in FIGS. 1 and 2 and depicting the mounting of a needle on the outer peripheral surface of the carrier and a resilient member carried within the carrier for locking a beard on the needle.

FIG. 3 is an enlarged view of needle sampler 100 in which needle roll 104 has rotated slightly clockwise with respect to hole 6 in sampling plate 5, thus more clearly revealing the initial sampling process for producing beard 102 at first Station L-L=Load and Lock. At this point, beard 102 is raw, ie, not yet prepared or conditioned for testing.

Key to the sampling concept is the insertion of needles 118 into protrusion 7 of fibers through hole 6 and then locking the sampled fibers onto needle 118 with elastomer 116 before further movement. Cam shaft 107 and machined flat 108 thereon are seen in FIG. 1 to be in position to permit needle 118 insertion and loading. That is, cam follower 111 and push rod 114 are retracted and needle 118 can penetrate fiber protrusion 7. In FIG. 3, cam shaft 107, which also rotates around axis 106, is seen to cause the elastomer 116 to be pushed against needle 118, thus locking the fibers. This loading and locking method enables acquisition of an unbiased sample of fibers 102 from batch 4. In some cases it is advantageous to employ a spring-loaded finger 23 to enforce better engagement and sampling. Finger 23 pushes the batch sample into hole 6 by means of spring 27. Finger 23 moves within body 25 which is attached to bottom plate 8 by cement if said plate is glass and by a screw or cement if bottom plate 8 is metal.

Tapered bundles 102, 103 in FIG. 2 are acquired as described above by one or more single needle and/or one or more multiple needle sampler modules 100, 101. In the rotary position shown in FIG. 2, the beards have been prepared for subsequent conditioning and testing and are no longer in the raw form, as seen in FIG. 1, when needle roll 104 is at the bottom. FIG. 2 reveals tapered beards 102, 103 when needle roll 104 has rotated approximately 180 degrees from Station L-L to be near top center. Two tapered beards 102, formed with two independent, single needle samplers 100, and tapered beard 103, formed with one multiple needle sampler 101, are shown. Apparatus and methods according to the invention may be utilized with only single needle samplers, only multiple needle samplers, or a mix. Practicalities dictate which one is best or when a mix is best.

Sample acquistion, preparation, conditioning, testing and disposal steps are effected at various rotationally-positioned stations around needle roll 104. These steps are effected by various assemblies whose design and operation are explained below. For emphasis, said stations and assemblies are contained within environmental enclosure 2, as noted at the outset. We shall revert to the important subject of Ultra Rapidly Conditioning the beards below.

To summarize this introduction, tapered beards 102 in FIGS. 1, 2 and 3 are subsamples acquired from a mass, or "batch" of staple fibers 4 pressed between top or sampling plate 5 and bottom plate 8. The beard 102 is acquired through a hole or holes 6 in sampling plate 5 by needles 118 in sampler module 100. Samplers 100, whose design and operation are explained above, move the sampled bundles 102 to subsequent steps or operational stations by rotational motion of needle roll 104. As seen in FIGS. 1 and 2, the raw samples 102 are first withdrawn or sub-sampled at Station L-L, or Load and Lock, when needle roll 104 is near the bottom, (FIG. 1), and then move around to the various stations. Note in FIG. 1 the section arrows 2—2 that define FIG. 2, where it is understood that the beards 102 are on the top and not yet drawn into URC-L assembly 200.

Before describing in detail certain of the other, subsequent and novel operations and assemblies, it is appropriate to overview the primary steps in the method and their relationship to the rotary motion imparted by needle roll or cylinder 104. (We use needle roll and needle cylinder interchangeably herein.) Note first and generally that needle cylinder 104 rotates about axis 106 and thus transports sampler modules 100. Shaft 107 may be viewed as stationary at this point in the description; however, note flat surface 108 on shaft 107, which acts as a cam lobe to actuate cam follower 111 of needle sampler module 100. The upper part 110 of sampler module 100 is fixed within needle cylinder 104.

At Station L-L=Load-Lock, as explained generally above and in more detail below, the raw beard specimen 102 is loaded and then locked onto the needle or needles in single needle sampler module 100. This and all subsequent operations are similar for multiple needle samplers 101.

At Station C=comb, excess fibers, neps, seed coat fragments, trash and the like are removed from beards 102 by comb 10. Comb 10 may be constructed of fillet wire, as known in the art. After passage of beard 102, comb 10 oppositely rotates about axis 12 to engage brush 14 where said excess fibers are removed from it.

At Station B=brush, the beard 102 engages brush 14. This brushing step further cleans and aligns the fibers and reduces crimp. After passage of beard 102, both comb 12 and brush 14 are rotated oppositely such that both are cleaned of excess fiber by suction nozzle 15. Both comb 12 and brush 14 are well known in the art and are driven by unshown gear motor and gear belt or other means. Suction is provided within nozzle 15 only when the comb 10 and brush 14 are rotating oppositely to the arrows indicated on FIG. 1.

At Station URC-L, the beards 102 are drawn into Ultra Rapid Conditioning and Length Measurement assembly 200 wherein the beard is further prepared, including ultrarapid conditioning of the fibers comprising the final sub-sampled and prepared beard, and wherein the length measurements are made. Both URC and Length measurements are described more fully below.

At Station STR=Strength, the strength measurements are made in assembly 300. This assembly is also more fully described below.

At Station R=Removal, any remaining fibers are removed from needle modules 100 by cleaning module 400. This removal is accomplished by rotating cam shaft 107 to a position R (FIG. 3) which unlocks the remaining fibers when needle roll 104 is at the removal station. Compressed air 421 and suction 422 aid the cleaning process.

Finally, needle roll 104 is returned to Station P=park, which is near Station L-L for the next measurement cycle. This "park" position, between completion of one measurement cycle and commencement of the next, is to be distinguished from other park positions during a measurement cycle.

It will be appreciated that the ultra rapid conditioning and length measurement steps at Station URC-L may be separated and be effected by two assemblies. Similarly, the operations at Stations URC-L, Str and R may be combined into a single, more complex assembly. Still further, some operations can, in some cases, be omitted. Showing them in the configuration of FIG. 1 facilitates disclosure of apparatus we have found to generally optimum for cotton. Testing other fibers could require different configurations of the same invention.

Whereas this invention is directed to measurement of fiber length and fiber strength, other measurements may be advantageously made substantially simultaneously as part of a fiber quality measurement system. When bottom plate 8 in FIG. 1 is glass, the color and trash of the bulk sample 4 may be determined by color scanner or camera means as disclosed in a co-pending application WO 01/20321. Scanner head 9 in FIG. 1 moves under bottom glass plate 8 to acquire said color images. If spring finger body 25 is attached to the glass window, that part of the image is ignored to avoid interference with measurement of the batch sample 4.

We now complete the detailed explanation of the elements, operations and procedures at Station L-L and next provide concepts and details for operations at Stations URC-L and Str, ie, with respect to assemblies 200 and 300.

In FIGS. 1, 2 and 3, needle sampler modules 100 are mounted in and rotatably transported by needle cylinder 104. Fiber mass 4 is pressed between a top plate 5 and a bottom plate 8 with an average pressure in the order of approximately 1 pound force per square inch of plate area (range=0.1 to 10 psi). Fiber types handled by the invention may be any textile staple fiber but this disclosure of our invention is particularly useful for staple fibers of cotton, wool, nylon or polyester.

Hole 6 in sampling plate 5, whose thickness is about 0.125 inch and whose material of construction is preferably stainless or hardened carbon steel, allows a protrusion of fibers 7. This protrusion of fibers 7, seen best in FIG. 3, presses against needle cylinder 104 and is engaged by needle sampler module 100 to form said tapered beard 102, in its raw, unprepared and unconditioned form. The size, shape and relationship of hole 6 to needle module 100 and needle cylinder 104 are important design parameters. When a single needle sampling module 100 is used, the hole 6 may be essentially circular, with diameter of about 0.4 inch. The minimum spacing between plate 5 and cylinder 104 is about 0.03 inch.

It is very important that hole 6 be champhered and smooth, especially in the leading edge area 11, otherwise fibers will be broken or pulled off the needle. At leading edge 11, the shape is actually rounded; that is, the sharp edge resulting from a bevelling or countersinking operation is made round and very smooth by hand filing and polishing with fine machinist's emery cloth. In some cases it is useful to have restraining needles 12 in the area of hole 6. One useful configuration for restraining needles 12 is that there be two of them situated on either side of sampling needle 118 path and spaced 0.200 inch apart. They should be 0.03 inch diameter and protrude into hole 6 by about 0.20 inches. Use of restraining needles 12 permits hole 6 to be larger and is more appropriate for long fibers than short.

The means by which fibers in beard 102 are "locked" onto sampling needle or needles in needle module 100 before further preparation was explained above. It will be appreciated from FIG. 2 that there may be a multiplicity of such needle modules 100 circumferentially around and/or axially along needle cylinder 104. It will also be appreciated that rows of closely spaced needles may be used, as in multiple needle sampler 101 in FIG. 2. Needle cylinder 104 is driven by motor 16 and its rotational position is measured by encoder 18. Needle cylinder may also be driven by a stepper motor system. All operational controls and measurements are handled by known microcontroller and PC means.

FIG. 3 shows needle sampler module 100 in enlarged cross sectional view and its relation to needle roll 104, axle 107 and cam flat 108. Cam follower 111 is driven by cam 108 into stationary part 110 and pushed out by spring 113. FIG. 3 shows the relationship of the components of sampler module 100 at Station L-L after the fibers 102 have been loaded onto needle 118 and elastomer 116 is closed by cam 108 action. Push rod 114 compresses the bottom side of elastomer 116 which in turn moves outward and presses against needle 118. The movement of push rod 114 is typically about 0.04 inch, which is the depth of cam flat 108, and the top side of elastomer 116 moves about 0.02 inch to envelop the fiber beard 102 when constrained as shown. Suitable materials for elastomer 116 are Buna-N and Viton and practical diameters are about 0.125 inch. The diameter of needle 118 ranges from about 0.02 to 0.06 inch. This topside movement is sufficient to lock beard 102 onto needle 118 for subsequent preparation and testing. Needle 118, which is hardened steel, is attached to stationary part 110, which is typically brass, by silver solder or by set screws, preferably.

Note in FIG. 3 the area 124 defined by the elastomer 116 topside, needle 118 bottomside, and the extension of milled surface 122. This area is adjusted so that the desired number of fibers in beard 102 are captured, which number for cotton, for example, is between a few hundred and a few thousand fibers. It will be appreciated that this number of sampled fibers is an important operational parameter. Note also that the top of stationary part 110 conforms to the contour of the needle roll 104.

We can now easily distinguish the instant invention from prior art mentioned above. U.S. Pat. No. 3,057,019 discloses a needle-based apparatus for sampling and preparing tapered beards. This well-known art is commonly referred to as the "Hertel" sampler and differs from the instant invention in five major ways. First, the Hertel sampler locks the fibers into the multiple needle structure after combing. The instant invention locks the fibers before combing. Second, the Hertel sampler locks the fibers between the needles and threaded grooves in a 0.5 inch bolt. Locking forces thus depend on needle alignments and amount of beard captured. The instant invention locks the fibers between the needles and an elastomer. Thus the instant invention enables more definitive locking and realizes a less-biased sample of fibers due, among other things, to fewer long fibers being lost.

Whereas the first two differences enable the instant invention to make better measurements of long fiber content, the third to fifth differences following enable better, indeed, "true" measurement of short fiber content. Third, the instant invention provides for single needle samplers 100 as well as a row of closely-spaced needles 101. The differences for short fiber content measurement relate to single needles, primarily. Fourth, the instant invention enables measurements of the beard much closer to the needles. Fifth, the state of fibers captured by single needles is far more definitive than for the Hertel sampler, since "cross-over" associated with multiple needles is eliminated. Cross-over refers to fiber ends which cross over two or more needles and then protrude outwardly. There is no "cross-over" with single needles. Thus the single needle configuration enables a true measurement of short fiber content which is not possible for the Hertel sampler.

It follows that the instant invention can provide the complete fiber length distribution since good data are available from short to long fibers in the beard.

It is noted for completeness that SFC measurements are currently attempted with Hertel type samplers using inference type "measurements." SFC data so produced are not true SFC and their accuracy and precision is widely known to be poor. As noted above, this is because very few of the short fibers are accessible for measurement due to proximity. Those that are accessible are in unknown states because of cross-overs.

It is finally noted, also for completeness, that SFC is one of the data products for which USDA and ITMF, as well as leading spinning mills and machinery manufacturers, are intensely soliciting improvements.

U.S. Pat. No. 5,491,876 discloses a multiple needle-based apparatus for individualizing single fibers for testing purposes. The preferred embodiment is an accelerated pin drafting device. U.S. Pat. No. 5,483,844, a divisional, discloses a single needle-based apparatus with elastomer locking, also used for individualizing single fibers. Neither of these prior art embodiments form and test a tapered beard. And neither the objectives nor methods of operation relate to or anticipate the instant invention.

Referring again to FIGS. 1, 2 and 3, it is seen that after the fiber beards 102 have been sampled (ie, loaded and locked) at Station L-L and prepared by combing and brushing at Stations C and B, they are transported to Station URC-L for Ultra Rapid Conditioning and for Length measurement. After length measurement, they are transported to Station Str 300 for strength measurement, which measurements particularly require proper conditioning. We next explain the features of URC, then explain Length measurement, both with assembly 200, and finally we explain Strength measurement, with assembly 300.

Figure 4:
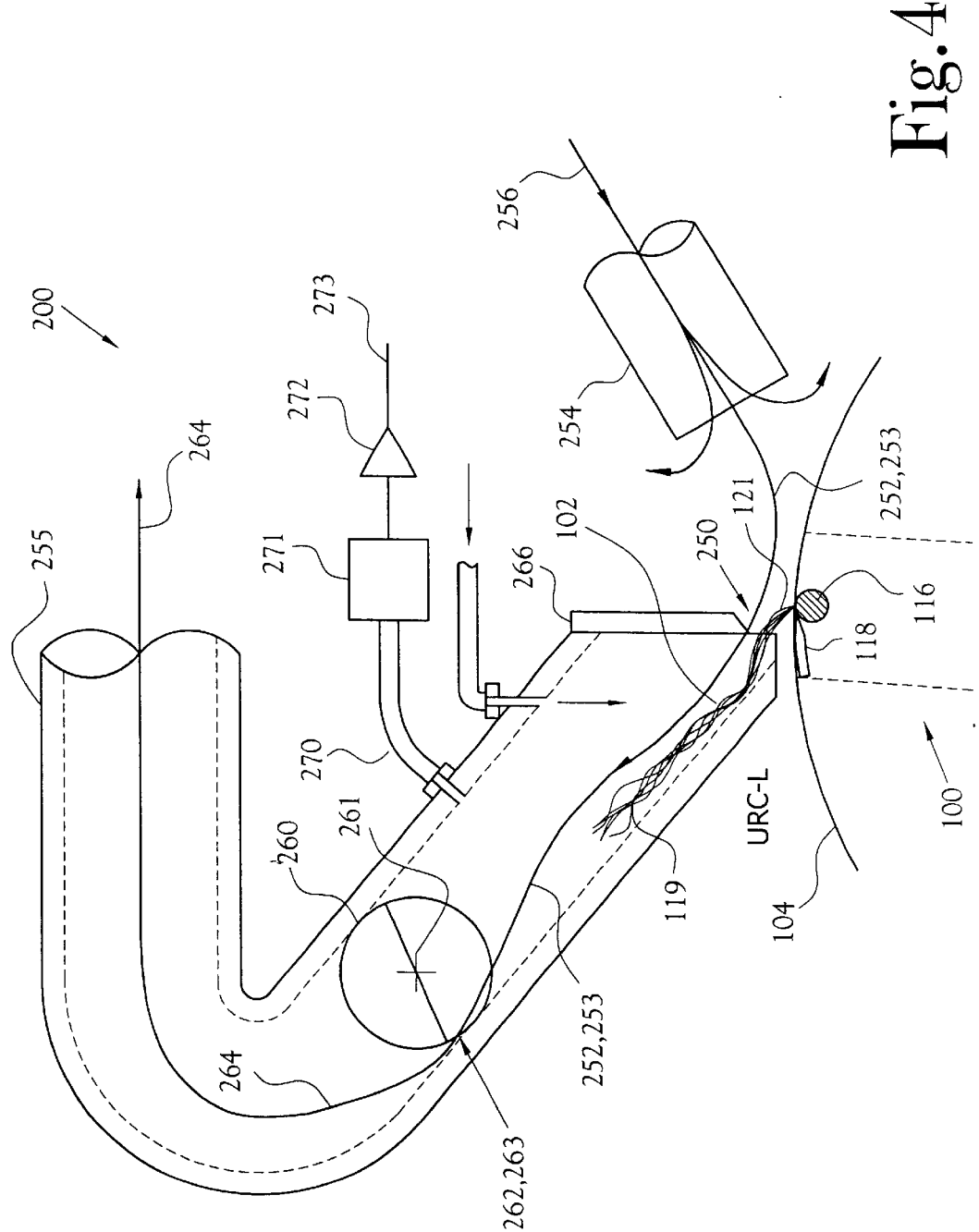
FIG. 4 is a representation of one embodiment of a test station embodying a flow channel for conditioned air for use in the apparatus depicted in FIG. 1.
Figure 5:
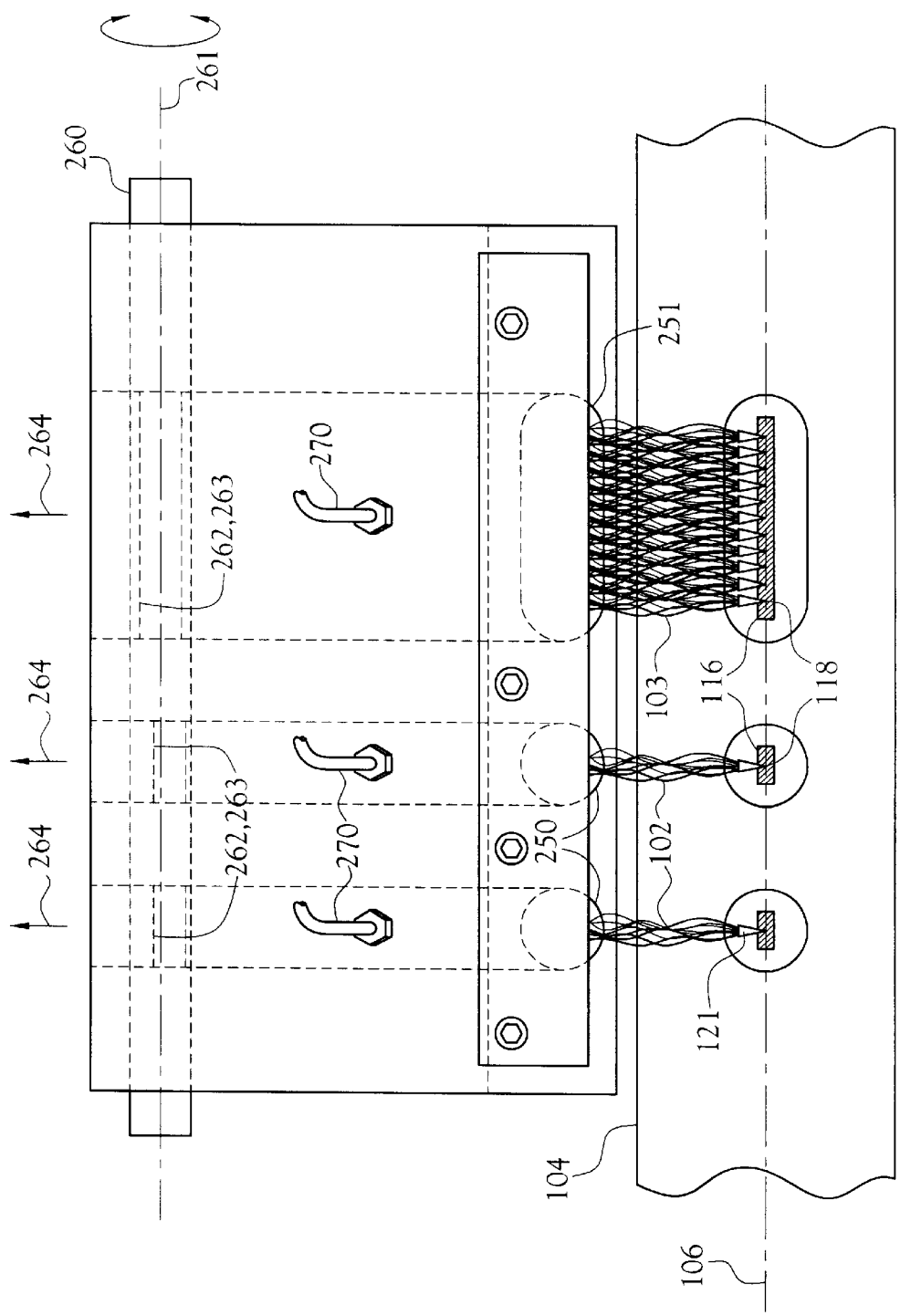
FIG. 5 is a representation of the entrance end of a flow channel as depicted in FIG. 4 and a needle-carrying carrier as depicted in FIG. 2.

In FIG. 4, an enlarged drawing depicting a first version of URC-L assembly 200, and in FIG. 5, the corresponding frontal view section 5—5, it is seen that needle roll 104 first transports the extreme ends or tips 119 of beards 102 past one of a plurality of first fixed orifices 250, 251 into which beard 102, 103 are drawn by increased suction flow 252. Increased suction flow 252, to be contrasted with reduced or measurement flow 253, results upon clockwise rotation of cylindrical and sealed plug valve 260 which produces a second, variable orifice 262, 263 by rotating about axis 261. For increased suction flow 252, variable orifice 262 is maximally open, in contrast with the more constricted position shown 263, thus maximizing the suction flow 252. After beard 102 is captured, as seen more clearly in FIG. 5, roll 104 reverses to permit beards 102 to penetrate maximally into fixed first orifices 250,251 in URC-L assembly 200, ie, near tapered beard base 121, and roll 104 parks as shown in FIG. 4. For reference, the width and height of single needle beard 102 first orifices 250 are approximately 0.4×0.04 inches. The width and height for multiple needle beard 103 orifices 251 are approximately 2×0.04 inches. The spacing between needle roll 104 and assembly 200 is about 0.025 inch.

Increased suction flow rate 252 would be typically about 5 CFM for each first orifice 250 for single needle tapered beards 102. The corresponding increased flow rate 252 for each first orifice 251 for multiple needle tapered beards 103 would be about 25 CFM. The driving suction 264 for either would be in the range of 25 inches water column. Some ultra rapid conditioning or testing circumstances require that first orifices 250,251 also be variable; it is obvious to those of ordinary skill in the art that this would be accomplished by making first orifice plate 266 movable, or the equivalent. Other URC applications require that the first 250,251 and even second orifices 262,263 be automatically controlled; such controls of the indicated and disclosed elements are also obvious to those of ordinary skill in the art.

Ultra rapid conditioning takes place when the beards 102, 103 are maximally penetrated into assembly 200. Initial conditioning occurs when the flows are high 252 and final conditioning occurs when the flows are reduced 253. To better explain the URC and length measurement at reduced, or measurement flow 253, we next describe certain of the operational conditions without beards 102, 103 present. This will be seen to be an important design condition for both URC and for length measurement by occluded orifice flow 253 and differential pressure 270. Explanation is given for one single needle 100 and its associated orifice 250 but the principle is the same for multiple needles 101 and first orifices 251 therefor.

After the beard 102 is captured and the needle roll 104 is parked as seen in FIG. 4, plug 260 rotates back to produce a second, more constricted position 263, as illustrated in FIG. 4. In this position, the flow 253 into first, fixed orifice 250 is reduced to about 2 CFM, without fibers 102 present, for this design explanation. The corresponding suction 264 or differential pressure relative to atmoshere driving this flow would also typically be about 25 inches. The differential pressure, relative to atmoshere, 270 across orifices 250 is in the range of 4 inches water column, again without beards 102 present; this corresponds to a gas velocity of about 8,000 feet per minute through orifice 250. In the first orifice 250 and second orifice 263 configuration shown in FIGS. 4 and 5, the volumetric flow rate 264 is primarily set by second orifice 263 and is almost constant, independent of occlusion of orifice 263, for small occlusions. Thus the velocity in the occluded orifice 250 is actually higher (than the non-occluded condition), when tapered beards 102 are in it and thus occlude part of the open area. The amount of tapered beard 102 is measured by the differential pressure 270. This "Fibrogram" length measurement by air flow is explained more fully below. The focus of the disclosure at this point is on ultra rapidly conditioning beards 102 in URC-L assembly 200. As noted above, URC of beard 102 takes place both with increased flow 252 and measurement flow 253. It is sufficient for disclosure of the concept to explain the URC process for reduced or measurement flow 253.

Conditioned gas flow 256, whose flow volume is larger than that of suction flow 252 or 253, is provided under slight, ~2 inches WC, positive pressure via conduit 254 by known and novel environmental conditioning apparatus, next described. This (and other) conditioning gas flows are supplied to and taken from enclosure 2 in FIG. 1, which is appropriately insulated.

Figure 6:
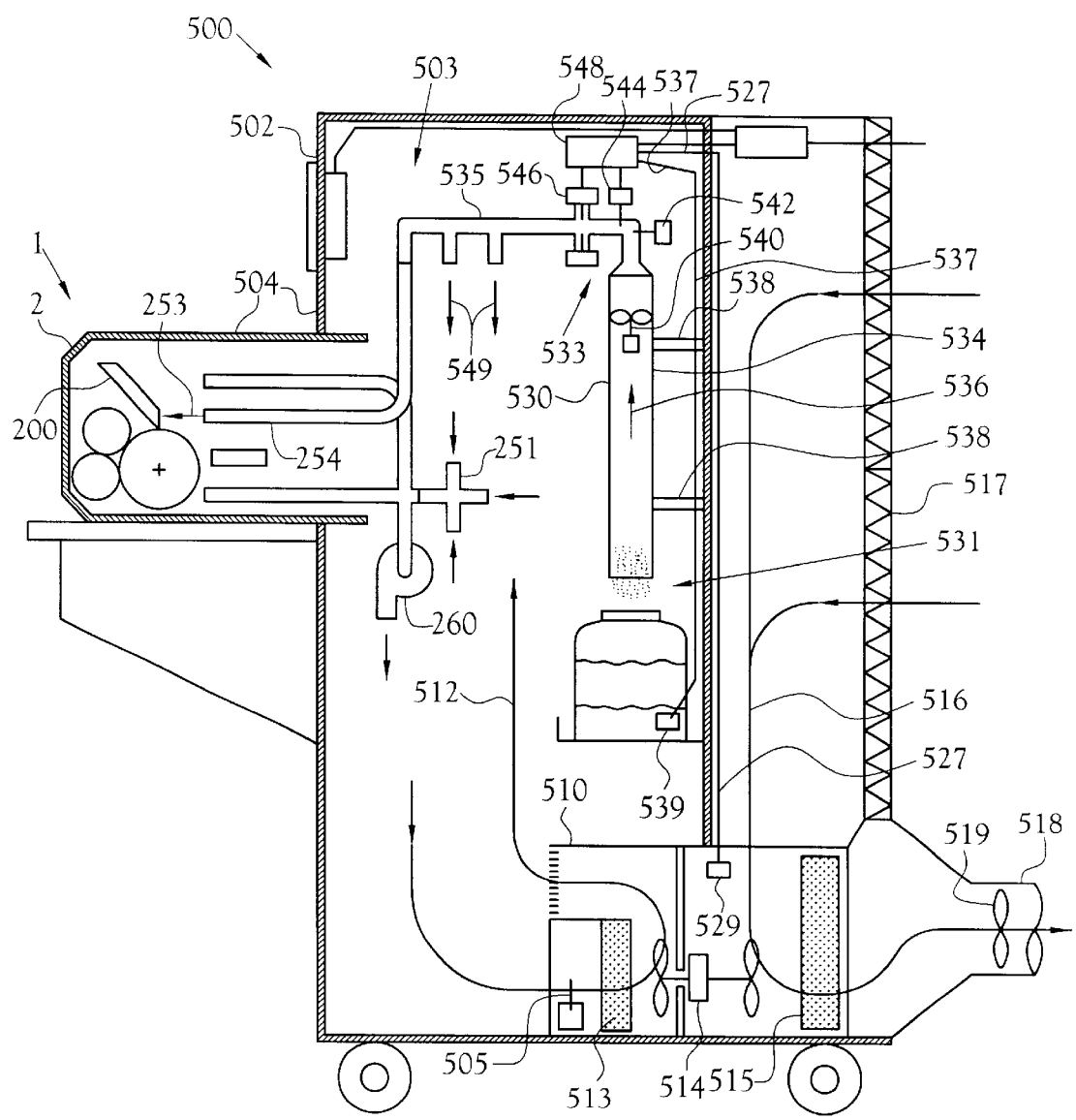
FIG. 6 is a schematic representation of one embodiment of apparatus for sampling and testing staple fibers in accordance with the present invention and depicting the relationship of the sampling and testing apparatus to a remote source of conditioned air.

FIG. 6 shows a RapidTester platform 500 with only L+Str module 1 and only such other elements, for clarity, as relate to this disclosure of Ultra Rapid Conditioning and L+Str measurements. It is understood that other measurement modules may be added to the RT platform and that some of them require URC as well. The principles disclosed here for L+Str apply to these other modules.

RT platform 500 consists of cabinet 502, part of which is provided with insulation 504. This insulated part is referred to as "MicroLab" 503 wherein ASTM test conditions of 65%

Relative Humidity and 70 degrees Fahrenheit=21 degrees Celsius, or other accepted test conditions, may be maintained by known thermal 510 and unknown or known humidification 530 air conditioning elements. Known air cooling/heating means comprise common room air conditioner 510 having cooled/heated flow 512 through coil 513. Heat is rejected/added by coil 515 into air flow 516. Both flows 512, 515 are driven by a common motor 514 with separate fans. Air from outside RT 500 is drawn in through filters 517, through coil 515, and then returned via duct 518, aided when required by booster fan 519.

Note, with emphasis, that the temperature in MicroLab 503 can be controlled by thermostat 505 which is integral with AC unit 510. AC unit 510 is in every way conventional, well known and widely available and therefore inexpensive. Economic considerations apply heavily here Alternatively, AC unit 510 may be externally controlled in response to temperature sensor 542, via microcontroller 548 to interface 529. In some cases, the extra cost and complexity are justified. Heat rejection capacities of the order of 8,000 BTU/Hour are typical. Because of internal heat load, heat addition is normally not needed but if the environments external to RT 500 were very, very cold, reverse cycle heating capacities of AC unit 510 of 4,000 BTU/hour would be adequate.

Unknown and known humidification means 530 are comprised of common, well known and widely available ultrasonic humidifier, which is also chosen for reasons of economy. Before explaining the novel features, it is appropriate to note that, for some applications, these known humidification means may be used to control relative humidity in the MicroLab, in combination with thermal control by AC unit 510 and in analogy therewith. That is, the humidistat integral with humidifier 532 can be used to control RH in the MicroLab. However, in practice, because in the typical case when AC unit is cooling, coil 513 is well below the dew point associated with 65%, and accordingly strips out water from flow 512 by condensing it on coils 513. Typically, the RH of air flow leaving 512 AC unit 510 can be as low as 35%. The deficit between this value and the desired set point 65% has to made up with humidification means such as ultrasonic humidifier 532. Whereas in some cases this is achievable, it is not generally, so with respect to ultra rapidly conditioning tapered beards 102,103 in the L+Str module, novel means of delivery and control are applied, as follows.

Aerosolized water particles 531 emitted from humidifier 532 are drawn into vertical tube 534 and transported by air flow 536 through monitoring station 533 and to distribution header 535. Air flow 536 is conditioned in temperature by AC unit 510, as explained above, and is propelled by fan 540. Humidification apparatus 534 is attached to cabinet 502 by brackets 538. At monitoring station 533 the temperature 542, relative humidity 544, and aerosol concentration 546 are measured by the indicated sensors and the readings are reported or input to microcontroller 548. Temperature 542 and humidity 544 sensors are widely available and known in the art. Humidity sensor 544 enables determination of either relative or absolute humidity; in this application we require the latter, so that the total water delivered via header 535, in both gaseous and aerosol forms, is known. Aerosol concentration sensor 546 is manufactured by ppm, Inc, Knoxville Tenn., a sister company to Schaffner Technologies. The aerosol concentration, in combination with volumetric flow rate 536, enables determination of the portion of water delivered to header 535 that is particulate in form. Microcontroller 548 sends or outputs signals on control line 537 to an interface element 539 within humidifier 532 to turn it on and off or to continuously modulate emissions 531. Similarly, if needed, microcontroller 548 outputs to control line 527 and to interface element 529 within AC unit 510 to control temperature. The novelty of our invention lies in the control of water, including which portion is in gaseous and which portion is in particulate form, that is delivered to L+Str module 200. As desired, communication between various elements associated with the platform 500 of FIG. 6, including the microcomputer 548 maybe be communicated through a known industrial computer 560 and line 562 to any of a plurality of external locations, such as a printer, display, etc., as is known in the art. Input to the computer 560 may include commands entered via a touch screen 501, for example.

As recited in co-pending application "Conditioning and Testing Cotton Fiber," WO 01/20321, we have determined that delivery of gaseous or molecular water alone fails to achieve equilibrium moisture content or equilibration of physical properties, such as length and strength, as rapidly as needed today. To solve this basic problem for testing or for processing, we discovered that delivery of a combination of water in molecular form plus aerosolized water particles enables equilibrations in seconds, not minutes. Key to this performance is delivery at high air velocities, so that the particles are impacted, uniformly, into the fibrous mass. As noted above, the air velocities within first orifices 250,250, FIGS. 4 and 5, are typically above 8,000 feet/min. These velocities are another order of magnitude higher than those recited in WO 01/20321 so it follows that impaction of such aerosolized water particles, as delivered to header 535 and to flow 253 by pipe 254 and into URC-L assembly 200, are very effective in ultra rapidly conditioning beards 102,103.

In co-pending application WO 01/20321 we also disclose that ultra rapid conditioning of more or less flat, thin "Classer's Samples" weighing of order 10 to 20 grams can be effected in minutes or fractions thereof because, primarily, the conditioning air velocity is in the range of hundreds to thousands of feet per minute. With respect to our further investigations, we have found that tapered beards 102 weighing of order 5 milligrams, when the conditioning gas velocity is in the order of 10,000 feet per minute can approach moisture content equilibrium in seconds and fractions of seconds. We also call this URC, even though it occurs an order of magnitude faster than our own prior art URC invention.

Besides being delivered to URC -L sub-assembly 200 in volumetric flow rates 253 of approximately 2 CFM and at velocity of about 8,000 feet/min within first orifices 250, the water delivered to URC-L assembly 200 may be further described as follows: total RH=65%; between 5 and 80% in aerosol form, with the aerosols having mass median diameter of about 15 micrometers and a particle size distribution having geometric standard deviation of about 2.0. When so delivered, moisture content and other physical measurement equilibration times of less than 10 seconds are achievable.

Implicit to these discussions is the idea that the beards 102, 103 always have to increased in moisture content. Although receipt of batch samples 4 which have the nominal 7.3% moisture content or higher does occur, it is very rare. But when it does occur, the beards are inherently dried by the sampling and combing-brushing process, so remoisturization is almost always required. It follows further that the remoisturization is from the "dry side," thus minimizing moisture content hysteresis effects.

Note that other deliveries 549 are available from header 535. Suction flow 253 is driven by blower 260 which provides other flows via manifold 251. Blower 260 is switched off when suction to L+Str assembly 200 or to other deliveries 261 is not needed. This doubly saves energy, since the power to blower 250 does not have to be rejected by AC unit 510.

We close this material on Ultra Rapid Conditioning by distinguishing it with respect to known prior patent art. Comments above already distinguish conditioning tapered beards 102 of cotton fibers, weighing typically 5 milligrams each, for single needle 100 beards, and multiple needle 101 beards, weighing typically 50 mg, with gas velocities of order 10,000 feet/min from conditioning thin samples weighing 10 to 20 grams with air flows of order 1000 feet/min, as disclosed in WO 01/20321.

U.S. Pat. No. 6,029,316 discloses methods and a machine for "rapidly" conditioning so-called "Classer's or HVI Samples" of cotton fiber, weighing of order 100 to 300 grams, not milligram tapered beards. Said rapid conditioning is prior to and physically separated from testing, with conditioning in times of order 15 minutes, not seconds. High velocities and controlled portions of aerosolized water deliveries are not used therein. U.S. Pat. No. 5,537,868 discloses conditioning the "Testing Zone" of fiber quality measurement instruments with separate, movable, and otherwise known air conditioning methods. Key to that invention is the use of feedback from temperature and humidity sensors within one or more "Testing Zones" to control the known, separate, and movable air conditioning apparatus. No feedback from testing zones is used with the instant invention nor is known, separate, and movable air conditioning apparatus employed. Our present invention uses some novel air conditioning apparatus that is, importantly, integral with and internal to the instrument platform, by intentional design.

U.S. Pat. No. 5,361,450 discloses conditioning internal "Processing Zones" of processing equipment, not testing instruments, and with known air conditioning means. We comment for thoroughness that WO 01/20321 also addresses processing applications with our novel moisturizing means.

We now explain the principle of measuring fiber length distribution by our air flow method. Again we will focus on tapered beards 102 formed by single needle samplers 100, in FIG. 4. When beard 102 is fully penetrated into assembly 200 to base length Lb 121, as explained above for URC, the differential pressure 270 is increased, from a typical no-beard or zero case of 4 inches WC, to typically 6 inches WC for a 5 mg beard. Note that this corresponds to local velocity over the beards 102 of about 10,000 feet/min. Larger beards 102 yield higher delta p 270 and lighter ones yield lower. Evidently, this delta p 270 yields an electronic analog signal 273 that is approximately proportional to the linear density or fineness of that part of beard 102 which is in or, better, occludes the first orifice 250.

Whereas this amount versus length sensing employs nearly constant flow 264 and the amount analog 273 is proportional to delta p 270, we note that an alternative configuration wherein first orifice 250 is small compared to second orifice 263 (in measurement flow condition) may be used. In this configuration delta p 270 is nearly constant and high and one senses the flow 264 by sensing the lower differential pressure across second orifice 263. Both configurations provide the same amount versus length information and one or the other is chosen for practical reasons.

Figure 7:
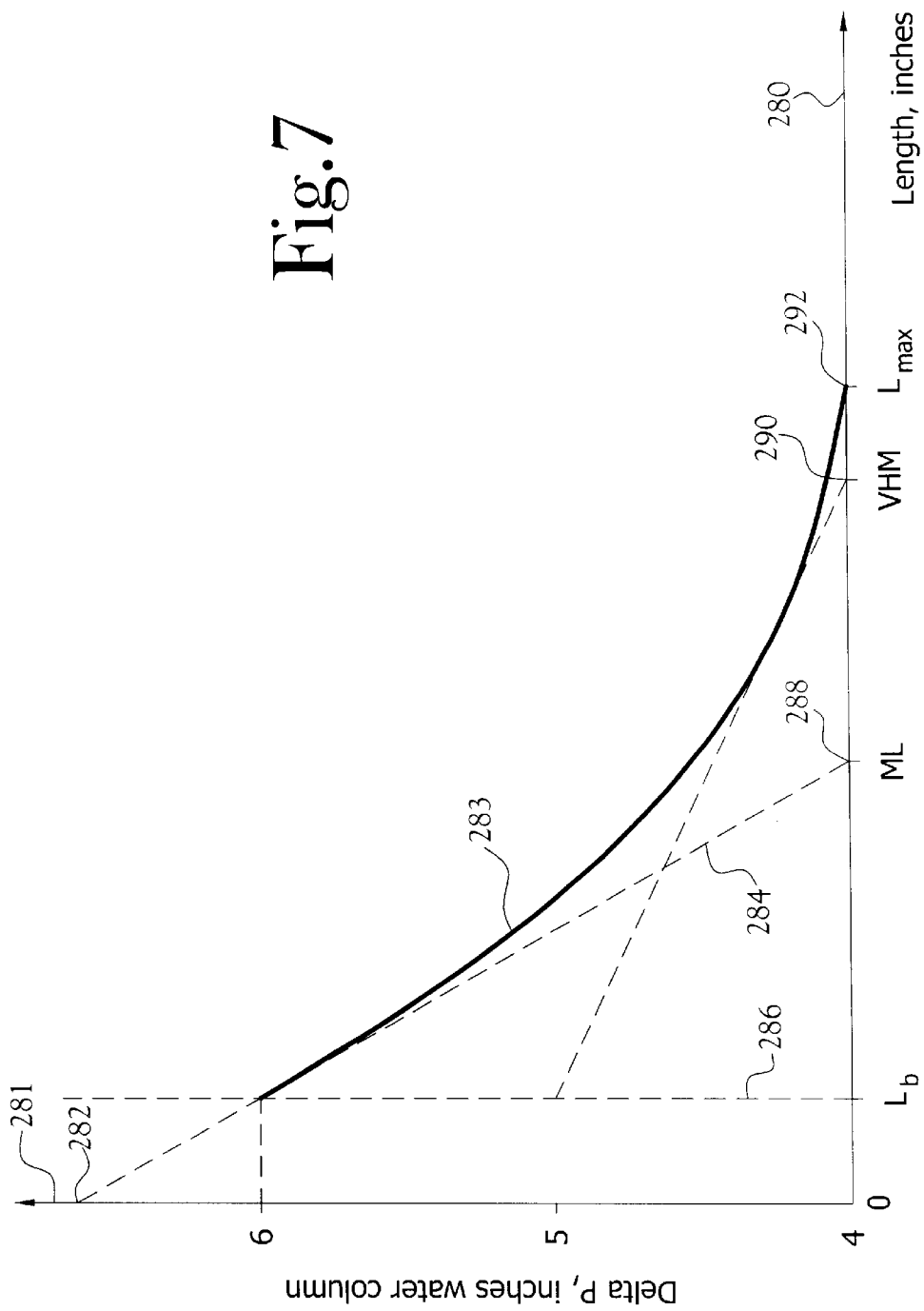
FIG. 7 is a graph plotting differential pressure versus length for a typical test of a beard.

After parking in the illustrated maximum penetration 121 of FIG. 4 for perhaps 10 seconds, during which ultra rapid conditioning time both increased 252 and measurement 253 flows are experienced, beard 102 is withdrawn from orifice one by precision rotation of needle roll 104. This angular movement is converted to true length withdrawn. During this withdrawal, variable orifice 263 is at lower, measurement flow 253 condition. The differential pressure 270 across fixed orifice 250 is recorded as a function of withdrawal length, thus effecting the well-known "Fibrogram" or beard amount versus length seen in FIG. 6. Differential pressure 270 is nominally in the range of 4 inches water column without beard 102 being inserted, as explained above; thus the baseline for the ordinate axis is seen to be 4 " to facilitate clarity. Normally the baseline is not shown. Pressure/vacuum transducer 271 and electronics system 272 yield analog voltage 273. As depicted in FIG. 7, a line 285 drawn through half the increment amount (6−4)=2×½, (at coordinates Lb and 5) and tangent with the amount versus distance response curve 283, intersects the abscissa, Length, of the graph at VHM, which is the Hertel's construction for the upper half mean. This known factor is recognized in the art and is deemed to be only an approximation. The peak value of the Delta P response, at maximum insertion of the beard into the test apparatus is noted at 281P.

The amount 283 signal, corrected as necessary to truly represent gravimetric fineness or linear density, is graphed with respect to amount 281 versus length 280 axes. We have determined that these corrections are quite constant and thus show delta p as the ordinate 281 variable. The amount signal is defined from the base length 121 FIG. 4 or Lb 286 FIG. 6 to Lmax 292, the longest fibers present. The abscissa 280 is shown as length in inches; it is to be understood that the precision movement of roll 104 is actually in angular measure provided by encoder 18 of FIG. 1 and that the proper conversions to length have been applied. Such conversions include simple geometric corrections for the variable angles that beard 102 makes with respect to first orifice 250 in FIG. 1. Length resolutions of order 0.005 to 0.010 inch and 12 bit A/D converter resolutions may be used in concert with known industrial personal computer hardware and software to automatically produce the length data products, representative ones of which are shown on FIG. 6 and next explained.

Mean fiber length=ML 288 is seen to be the tangential extrapolation 284 into the length axis 280 from the minimum length point Lb 286 and maximum amount 281. Upper Half Mean Length=UHM 290 is seen to be the tangential extrapolation into the length axis 280 from 50% of the maximum amount value at the base length Lb 286. These approximations were developed by Hertel in the 1940s. It follows that the complete fiber length distribution can be determined by such treatments of the basic amount versus length data, especially including short fiber content, for which improved results with the instant invention are enabled by smaller base length Lb 286 and more definitive extrapolations to zero length 282.

Figure 8:
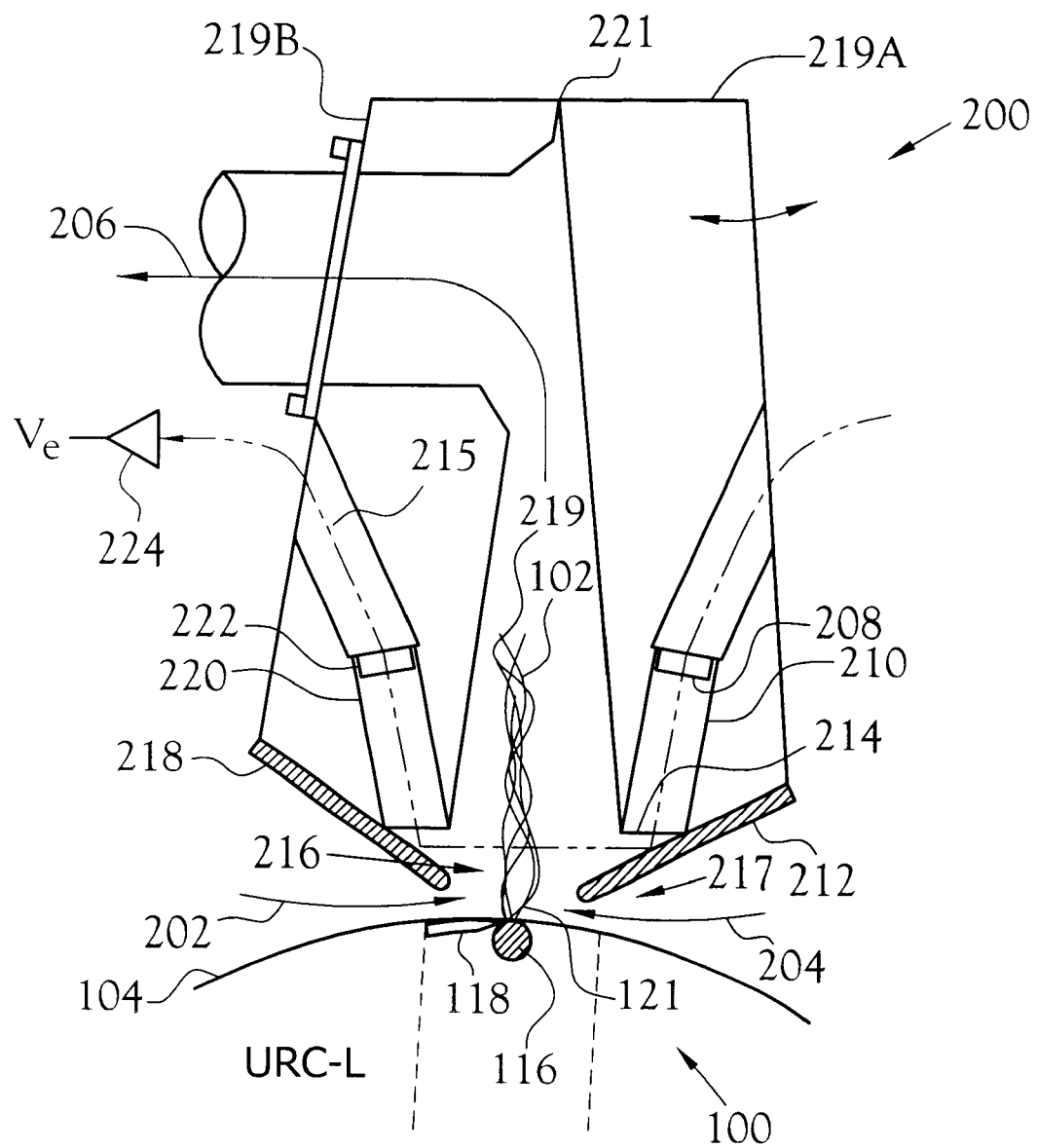
FIG. 8 is a schematic representation of an alternative embodiment of a URC-L subassembly.

FIG. 8 discloses an alternative URC-L station and assembly 200. The URC means are substantially the same as disclosed above but the amount versus distance or Fibrogram sensing means are electro-optical, not pneumatic. In FIG. 8 it is seen that beard 102 is drawn into sensing zone 217 of Length measurement apparatus 200 by inlet air flows 202, 204 which are enabled by suction flow 206. Total suction flow 206 is typically 5 CFM. Since the air velocity is high and the beard 102 consists of only a few hundred to a few thousand loosely related fibers, the fibers condition very rapidly, in a few seconds typically, to proper equilibrium moisture contents for testing, as explained above. This means that inlet air flows 202, 204 can be controlled in relative humidity, with both aerosol and molecular forms of water, and temperature to correspond to equilibria associated with standard testing conditions of 65% and 70 degrees Fahrenheit by means disclosed above.

After this "ultrarapid" conditioning step, jaw assembly 200 is partly closed, such as by rotating movable section 219A about axis 221 by unshown but known actuation, but without clamping the fibers. The left section 219B remains fixed. Needle cylinder 104 moves clockwise to pull the fiber beard 102 out and around mirror/nose piece 212. Nose piece is typically within about 0.03 inch of roll 104. It is seen that near proximity of the sensing zone 217 to the base 121 of beard 102 is hereby accomplished. This is important for measurement of short fiber content. The movement of roll 104 is precisely measured, typically with resolutions of a few thousandths of one inch. Such precision is enabled with encoder 18 seen in FIG. 2 or by use of stepper motors.

While the beard 102 is being withdrawn, an extinction mode electro-optical sensor signal Ve is produced by detector 222 and amplifier 224 combination. This Ve signal is related to the "amount" or fineness of beard 102 and the basic amount versus length data are plotted and analyzed in the same manner as shown in FIG. 7 and in the text related thereto.

Completing the extinction mode sensor are laser or LED light source 208, mirrors 212, 218 and various apertures 214,216 and passageways within assembly 200, and detector 222 and electronics 224. These elements plus central ray 215 define the fundamental features of the extinction mode sensor with sensing zone 217.

It will be appreciated that combinations of the pneumatic and electro-optic amount versus distance sensing means may be advantageous. Pneumatic sensing is better for short fiber content and electro-optic is better for long fiber content. It will also be appreciated that other amount sensing means, such as electrical conductance, both resistive and capacitive, may be used for amount sensing with our invention. Electric conductance has the significant merit that the moisture content of the beards may be sensed. This moisture content sensing has both control dimensions and data product dimensions. That is, the actual moisture content of the beards can be reported as part of the archived records about the fiber quality testing.

Figure 9:
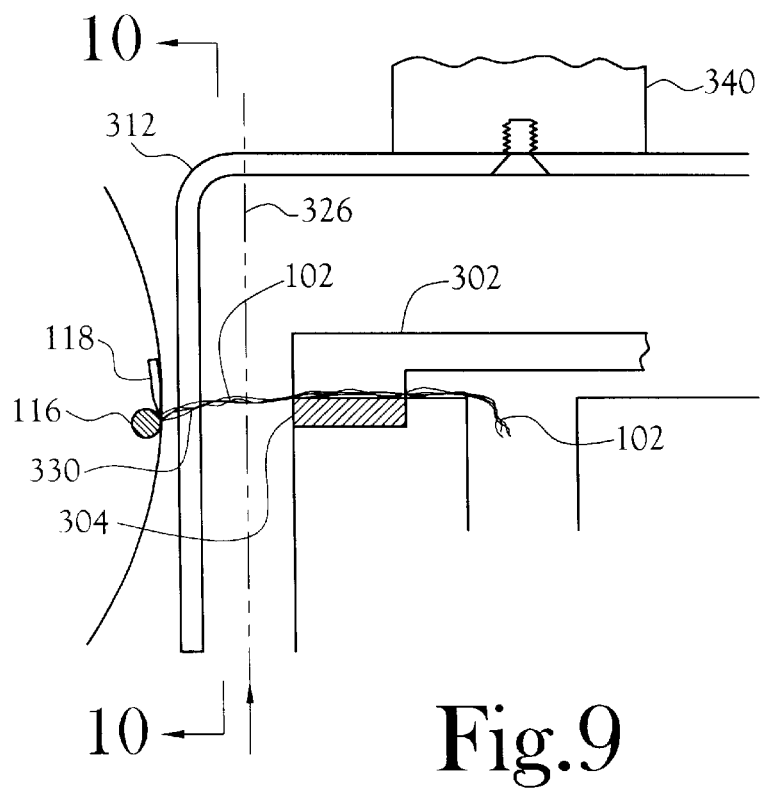
FIG. 9 is a partial schematic representation of a strength testing subassembly useful in one embodiment of the present invention.

We finally disclose the operations and measurements at Strength Station Str, with reference to strength measurement assembly 300, seen in FIGS. 1 and 9. In FIG. 1, moving jaw 302 is shown open. Suction is applied to pipe 308, and is provided, for example, by one of the connections to manifold 251 in FIG. 6, thus causing capture and conditioning flow 310. When needle roll moves to Str position, and beard 102 is moved to entry position 320, beards 102, which have been sampled, prepared and conditioned at previous stations, are drawn into open jaws 302 and 304 by suction flow 310. Needle roll 104 then backs up to either allow maximal penetration of beard 102 into Str assembly 300 or to such other penetration depth as desired.

one such alternative penetration depth is 0.125 inch, which is a common "gauge length" for fiber bundle strength testing. This ⅛ inch is measured from the back side of needle 118, over the smooth surfaces 330, 331 of fingers 312, 313 to the front of clamp 302. Another penetration depth procedure is to insert the beard 102, 103 until a fixed amount is realized, resulting however in variable gauge.

After reaching the selected position for testing, moving jaw 302 rotates around axis 305 and clamps beards 102, onto jaw liner material 303 which is mounted into stationary jaw 304, as best seen in FIGS. 1 and 9.

Figure 10:
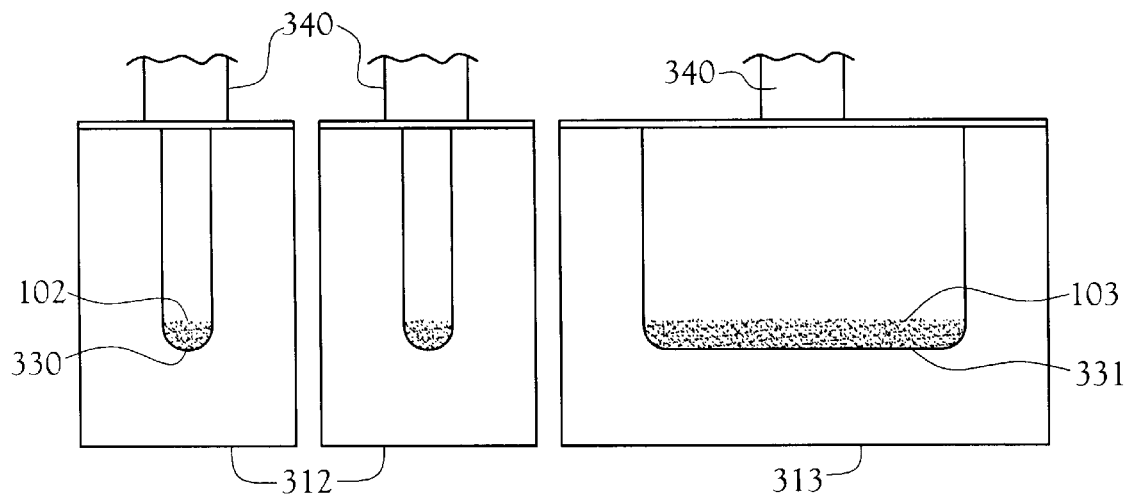
FIG. 10 is a backside view of load fingers along taken generally.

FIG. 10, whose section line 10—10 is seen in FIG. 9, shows how tapered beards 102 and also 103 engage the smooth surfaces 330, 331 of load fingers 312, 313 just after said beards 102, 103 are drawn into assembly 200 and jaws 302, 304 are closed, but before the force-elongation test is executed.

Referring again to FIGS. 1 and 9, it is seen that simultaneously with production of force-elongation data the "amount" or fineness in tex of the beard is acquired from an optional extinction mode electro-optical system comprised of laser or LED source 322 and detector 324. Centerline ray 326 and electronics 328 define the system, which is seen to be functionally identical with the embodiment disclosed in FIG. 8. The ratio of peak force divided by amount is beard tenacity or strength, conventionally reported in grams force/tex amount. Provision of actual amount remaining during the force-elongation break will be appreciated as an important novelty which enables greater precision in the tenacity measurement. We note that the amount versus length information for each beard, but without any tension, is already available from the length measurement station 200. It can be appreciated from this discussion that the length station can be combined with the strength station, as noted at the outset, when practicalities dictate, and that length can be measured by pneumatically, electro-optically, or electrically sensing amount versus length.

Referring particularly now to FIG. 9, and noting the defintion of ⅛ gauge above, it is seen that as needle roll 104 rotates clockwise, thus elongating the beard 102, that the tension in said beard 102 causes a downward force on load finger 312. This force component is sensed in relation to the moment arms L1 and L2 seen in. FIG. 1, as force transducer 340 is attached to load finger 312 and rotates about fixed and weakened end 313.

Figure 11:
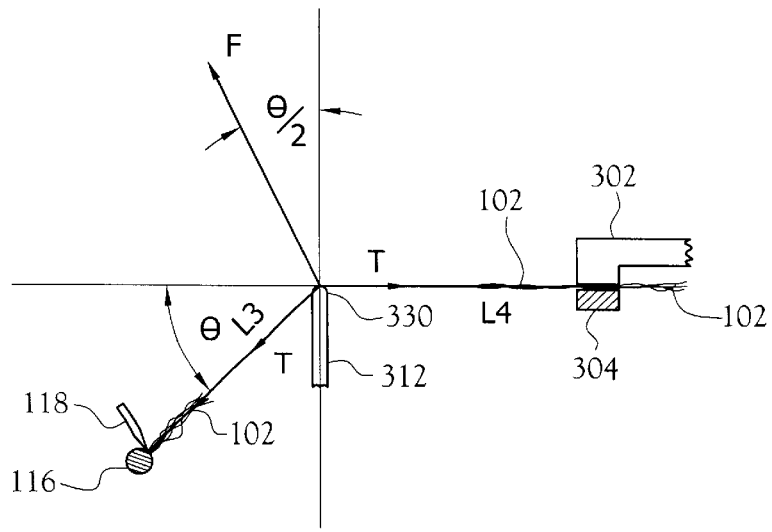
FIG. 11 is vectoral diagram depicting certain of the parameters applicable in a typical fiber strength test employing the concepts of the present invention.
Figure 12:
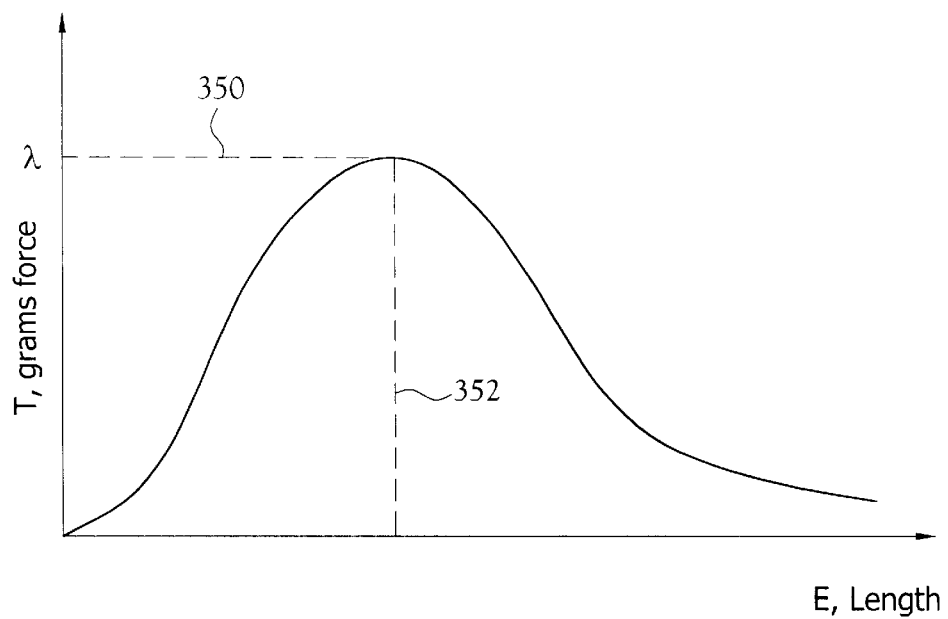
FIG. 12 is a graph plotting tension versus elongation (length) for a typical strength test of a staple fiber beard employing the concepts of the present invention.

FIG. 11 shows the vector diagram of forces acting on beards 102, 103 being clamped by needle 118 and jaw 302, 304 and at gauge length=L3+L4. T is the tension in the beard and F is the force applied to the beard as it passes over finger 312. The vertical component of F is sensed by load cell 340 as signal 342, as properly amplified and conditioned by electronics 343, as ratioed by moment arm lengths L1 and L2 seen in FIG. 1, and as corrected for the angle theta seen in FIG. 11. The resulting tension T versus elongation E (ie, corrected length) diagram is seen in FIG. 12. By corrected length we note that geometric corrections must be made to the rotary motion of needle roll 104. We further note that these corrections, which are completely straightforward, are more significant for the strength measurement is assembly 300 than for the Length measurement in assembly 200.

The final strength data product is the ratio of maximum tension 350 divided by the amount at known gauge length, in grams force per tex. Elongation, normally expressed as % of the initial gauge length, is length at peak load 352 divided by initial gauge length×100% is another data product produced at strength station 300.

We note in conclusion that length and strength-elongation data products are produced for each single needle 100 or multiple needles 101 and that these results are combined for reporting the length-strength properties of the samples 102, 103 from the batch 4.

While the present invention has been illustrated by description of several embodiments and while the illustrative embodiments have been described in considerable detail, it is not the intention of the applicant to restrict or in any way limit the scope of the appended claims to such detail. Additional advantages and modifications will readily appear to those skilled in the art. The invention in its broader aspects is therefore not limited to the specific details, representative apparatus and methods, and illustrative examples shown and described. Accordingly, departures may be made from such details without departing from the spirit or scope of applicant's general inventive concept.

Having thus described the aforementioned invention, we claim:

1. A method of ultra-rapidly conditioning a sample of staple fibers comprising the steps of withdrawing a bundle of staple fibers from a batch of the staple fibers, converting said bundle of staple fibers into a tapered beard of staple fibers, said beard having first and second opposite ends, and thereafter subjecting said tapered beard of staple fibers to conditioned air flow moving in a direction from said first end of and along the length of said beard for a time sufficient to condition said beard for testing.

2. A method of extracting a sample from a quantity of contained staple fibers comprising the steps of providing a containment for the staple fibers wherein the containment includes an opening defined through one wall thereof and the fibers contained therein are presented to said opening in bulk, rotating a needle roll bearing at least one needle sampler exposed on the outer peripheral surface of said needle roll past said opening, capturing a bundle of fibers from said containment with said needle sampler, transporting said bundle of fibers captured on said needle sampler through at least one physical conditioning station wherein said bundle of fibers is converted to a fiber beard having first and second opposite ends and comprising a plurality of staple fibers which are substantially aligned in a common direction, transporting said physically conditioned fiber beard to a testing station, while disposed within said testing station, subjecting said beard to conditioned air flowing at ultra-high velocity in a direction from said first end of and along the length of said beard for a time sufficient to condition said beard for testing, determining at least one property of said fibers of said beard, withdrawing said beard from said testing station, and separating said beard from said needle sampler.

3. The method of claim 2 wherein said fibers of said beard are tested for their length.

4. The method of claim 2 wherein said fibers of said beard are tested for their strength.

5. The method of claim 2 wherein said conditioned air flows over said beard at a velocity of multiple hundreds of feet of per minute.

6. The method of claim 2 wherein said beard comprises about 5 mg of staple fibers.

7. The method of claim 2 wherein said air flow over said beard is continued for a time of at least 10 seconds but less than one minute.

8. In a method of sampling a batch of staple fibers the improvement comprising containing the batch of staple fibers within a container having a wall thereof within which there is defined an opening through said wall, urging the fibers of the contained batch of staple fibers toward said opening to the extent that the a portion of the fiber protrude from said opening, moving a collector past said opening, said collector capturing a bundle of said fibers and withdrawing the same from the batch of staple fibers through said opening, and anchoring said bundle of fibers to said collector, converting said bundle of fibers into a tapered beard of fibers, and conditioning said fibers of said beard preparatory to testing of at least one property of said fibers.

9. The method of claim 8 and including the step of testing the length and strength of said fibers of said beard without removal thereof from said collector.

10. The method of claim 9 and including the step of removing said beard from said collector.

11. Apparatus for the collection of a sample quantity of staple fibers from a batch of the staple fibers comprising a container housing a batch of staple fibers, said container including a wall member having at least one opening extending therethrough, said container including means urging said batch of fibers in the direction of said opening in said wall member, a carrier having an outer peripheral wall and being mounted for rotation about a central longitudinal axis thereof, a collector mounted in said outer peripheral wall and projecting therefrom by an amount sufficient to cause said collector to engage and withdraw a sample quantity of the staple fibers upon rotation of said collector past said opening upon rotation of said carrier, and means anchoring said withdrawn quantity of staple fibers on said collector, a resilient member carried by said carrier in a position proximate to said collector, and means selectively biasing said resilient member into engagement with said quantity of staple fibers on said collector.

12. The apparatus of claim 11 wherein said means for selectively biasing said resilient member comprises a shaft mounted for movement between positions of operative and non-operative engagement with said resilient member and cam means operatively engaging said shaft for selectively moving said shaft toward its position of operative engagement with said resilient member.

13. The apparatus of claim 12 and including telescoping housing elements defining a mounting structure for substantially unrestrained movement of said shaft within the confines of said housing elements and spring means biasing said telescoping housing elements toward minimum telescoping relationship therebetween, one of said housing elements being interposed between said shaft and said cam.

14. The apparatus of claim 11 wherein the fibers are urged toward said opening to the extent that a portion of the fibers protrude through said opening and said collector includes a needle type projection on said outer peripheral surface of said carrier, said projection being adapted to be moved past said container of fibers and to engage and withdraw a sample quantity of staple fibers from said container through said opening.

15. The apparatus of claim 11 wherein said means for anchoring said sample of stable fibers on said projection is mounted on said carrier in operative juxtaposition with said projection and thereby movable simultaneously with said projection.

16. The apparatus of claim 11 and including means for converting said sample of fibers to a tapered beard of said fibers, means for ultra-rapidly conditioning said fibers of said beard for testing, and means for testing at least the length and strength of said fibers of said beard.

17. The apparatus of claim 11 wherein said fibers remain attached at one end thereof to said collector, hence to said carrier, throughout their conversion to a tapered beard, their conditioning and their testing.

18. The apparatus of claim 17 wherein rotational movement of said carrier conveys said collected sample of fibers sequentially through their conversion to a tapered beard, their conditioning and their testing.

19. The method of claim 17 and including the step of measuring elongation of the fibers as the incremental relative movement of said sampling needle and said jaw, divided by the initial gauge.

20. The apparatus of claim 11 wherein said carrier comprises a generally hollow cylindrical housing having an outer periphery and a longitudinal axis, means mounting said housing for rotation about its longitudinal axis, hence rotation of said outer periphery of said housing past said opening in said container.

21. The apparatus of claim 11 wherein said outer peripheral surface of said carrier includes a milled cavity and said collector resides substantially within said cavity.

22. The apparatus of claim 21 wherein at least a portion of the fibers protrude into said milled cavity in position to be engaged by said collector.

23. Apparatus for testing the length of the fibers of a tapered beard of the fibers comprising a carrier having an outer peripheral surface and mounted for rotation about a longitudinal axis of said carrier, a tapered beard of staple fibers having a first end anchored to said outer peripheral surface of said carrier and a second end comprising unsupported ends of those fibers anchored to said carrier, an elongated air flow channel having an entrance and an exit, a source of conditioned air located remote from said elongated flow channel, first conduit means interposed between said source of conditioned air and said entrance to said flow channel and providing for the supply of conditioned air to said entrance to said flow channel, second conduit means interposed between said exit of said flow channel and said source of conditioned air and providing for the return of conditioned air from said flow channel to said source of conditioned air, whereby rotational movement of said carrier delivers said second end of said beard to the entrance to said flow channel whereupon said unsupported ends of the staple fibers of said second end of said beard are carried by the flow of conditioned air into said flow channel and retained in said flow channel for a time sufficient to condition said fibers of said beard.

24. The apparatus of claim 23 wherein said conditioned air is supplied to said entrance of said flow channel at a velocity of not less than about one hundred feet per minute.

25. The apparatus of claim 23 wherein said conditioning of said fibers of said beard is effected within less that thirty seconds.

26. The apparatus of claim 23 wherein said fibers of said bead are conditioned within less than fifteen seconds.

27. The apparatus of claim 23 wherein said first conduit means terminates proximate said entrance of said flow channel.

28. A method of measuring tenacity of tapered beards of staple fibers comprising the steps of:

forming at least one tapered beard of staple fibers disposed on a respective sampling needle with ends of respective ones of said fibers extending unsupported from said sampling needle, by intercepting protrusions of bulk samples of staple fibers from a perforated plate employing said respective sampling needle, locking said tapered beard onto said needle, combing said beard while said beard is locked on said needle, brushing said beard while said beard is locked on said needle, conditioning said fibers of said beard during at least one of beard formation, beard preparation, or fiber measurement operation, measuring tex versus length of said fibers of said beard, clamping said unsupported ends of said fibers of said beard in a jaw system, while maintaining said jaw system rigid, moving said sampling needle away from said jaw system, measuring the peak force and displacement of said fibers within the space between said needle sampler and said jaw system, and combining the fiber tex and peak force to provide tenacity in grams peak force per tex.

29. The method of claim 28 and including the step of calibrating said tenacity measurement in terms of known tenacity values.

* * * * *